United States Patent
Nikolajsen et al.

(10) Patent No.: US 11,852,570 B2
(45) Date of Patent: Dec. 26, 2023

(54) METHOD FOR PREPARING A SAMPLE FOR LASER INDUCED BREAKDOWN SPECTROSCOPY

(71) Applicant: Foss Analytical A/S, Hilleroed (DK)

(72) Inventors: Thomas Nikolajsen, Hilleroed (DK); Daniel Aden, Hilleroed (DK)

(73) Assignee: Foss Analytical A/S, Hilleroed (DK)

( * ) Notice: Subject to any disclaimer, the term of this patent is extended or adjusted under 35 U.S.C. 154(b) by 0 days.

(21) Appl. No.: 18/158,054

(22) Filed: Jan. 23, 2023

(65) Prior Publication Data

US 2023/0160792 A1    May 25, 2023

Related U.S. Application Data

(63) Continuation of application No. 17/575,819, filed on Jan. 14, 2022, now Pat. No. 11,566,979, which is a (Continued)

(51) Int. Cl.
*G01N 1/28* (2006.01)
*G01N 1/44* (2006.01)
(Continued)

(52) U.S. Cl.
CPC .............. *G01N 1/286* (2013.01); *G01N 1/44* (2013.01); *G01N 21/718* (2013.01);
(Continued)

(58) Field of Classification Search
CPC .......... G01N 33/573; G01N 33/56911; G01N 33/0098; G01N 33/5044; G01N 33/505;
(Continued)

(56) References Cited

U.S. PATENT DOCUMENTS 3,586,511 A * 6/1971 Bishop ................... A23K 10/30
426/454
4,552,863 A 11/1985 Fujimori
(Continued)

FOREIGN PATENT DOCUMENTS

AU    2004264610 A1 * 1/2006 .............. C08L 63/00
BR    102013008531 A2    11/2014
(Continued)

OTHER PUBLICATIONS

International Search Report PCT/ISA/210 for International Application No. PCT/IB2016/055342 dated Jun. 8, 2017.
(Continued)

*Primary Examiner* — Michael P Stafira
(74) *Attorney, Agent, or Firm* — Harness, Dickey & Pierce, P.L.C.

(57) ABSTRACT

A method for preparing a sample of organic material for laser induced breakdown spectroscopy (LIBS) may include obtaining granular organic material, forming a portion of the granular organic material into a sample pellet, and searing the organic material. The searing may include searing only an exposed end surface of the sample pellet on which LIBS analysis is to be performed. The method may include pressing the seared sample pellet to consolidate the material comprising the seared end surface.

5 Claims, 3 Drawing Sheets

Related U.S. Application Data continuation of application No. 17/038,531, filed on Sep. 30, 2020, now Pat. No. 11,243,147, which is a continuation of application No. 16/323,572, filed as application No. PCT/IB2016/055342 on Sep. 8, 2016, now Pat. No. 10,830,674.

(51) Int. Cl.
*G01N 33/483* (2006.01)
*G01N 21/71* (2006.01)

(52) U.S. Cl.
CPC . *G01N 33/4833* (2013.01); *G01N 2001/2886* (2013.01); *G01N 2223/312* (2013.01); *G01N 2223/618* (2013.01); *G01N 2223/6126* (2013.01)

(58) Field of Classification Search
CPC .... G01N 33/5088; G01N 1/44; G01N 21/718; G01N 2223/618; G01N 1/286; G01N 2001/2886; G01N 2223/312; G01N 2223/6126; G01N 33/4833; G01N 27/44721; G01N 33/54393; G01N 33/57492; G01N 33/60; G01N 1/4044; G01N 2021/4709; G01N 21/03; G01N 21/3563; G01N 21/3577; G01N 2201/129; G01N 2223/612; G01N 2500/10; G01N 2800/065; G01N 2800/56; G01N 33/6857; G01N 33/6893; G01N 33/6896; G01N 33/74; G01N 35/00029
See application file for complete search history.

(56) References Cited

U.S. PATENT DOCUMENTS

| | | | |
|---|---|---|---|
| 6,682,667 B1 | 1/2004 | Matviya | |
| 7,663,749 B2 | 2/2010 | Levesque et al. | |
| 8,319,964 B2 | 11/2012 | Hahn | |
| 9,478,324 B1 | 10/2016 | Favetta et al. | |
| 2003/0021991 A1 | 1/2003 | Sugayoshi et al. | |
| 2005/0012244 A1* | 1/2005 | Jones | C08L 63/00 264/400 |
| 2005/0230872 A1* | 10/2005 | Scobee | A23N 5/01 264/141 |
| 2007/0020172 A1 | 1/2007 | Withers-Kirby et al. | |
| 2009/0062427 A1* | 3/2009 | Tornow | B29C 48/865 524/543 |
| 2010/0124583 A1 | 5/2010 | Medoff | |
| 2011/0083953 A1 | 4/2011 | Horn et al. | |
| 2014/0076167 A1 | 3/2014 | Boggavarapu | |
| 2014/0259895 A1 | 9/2014 | Mason | |
| 2015/0017313 A1* | 1/2015 | Zeeck | C10L 5/445 44/589 |
| 2016/0054284 A1* | 2/2016 | Washburn | G01N 21/718 356/318 |
| 2016/0091434 A1 | 3/2016 | Fagan et al. | |
| 2016/0349174 A1 | 12/2016 | Washburn | |
| 2019/0048307 A1 | 2/2019 | Morash et al. | |

FOREIGN PATENT DOCUMENTS

| | | | | |
|---|---|---|---|---|
| CN | 203385665 U | | 1/2014 | |
| CN | 205223318 U | * | 5/2016 | |
| DE | 102011017243 A1 | * | 10/2012 | ............. C10L 5/363 |
| EP | 1632770 A2 | | 3/2006 | |
| EP | 2589648 A1 | * | 5/2013 | ............. C10B 49/10 |
| GB | 2521278 A | * | 6/2015 | ........... C08K 11/005 |
| JP | 2007003510 A | * | 1/2007 | |
| KR | 20060135700 A | * | 12/2006 | |
| KR | 20150116501 A | | 10/2015 | |
| KR | 20160091185 A | | 8/2016 | |
| WO | WO-2011130804 A1 | * | 10/2011 | ................ G01J 3/28 |
| WO | WO-2014053083 A1 | * | 4/2014 | ............ B01D 53/02 |
| WO | WO-2015/082424 A1 | | 6/2015 | |
| WO | WO-2016/000072 A1 | | 1/2016 | |
| WO | WO-2016028658 A1 | * | 2/2016 | ............ G01J 3/0218 |

OTHER PUBLICATIONS

Written Opinion of the International Searching Authority PCT/ISA/237 for International Application No. PCT/IB2016/055342 dated Jun. 8, 2017.

Herring A M et al: "Detection of reactive intermediates from and characterization of biomass char by laser pyrolysis molecular beam mass spectroscopy", F, IPC Science and Technology Press, Guildford, GB, vol. 83, No. 11-12, Aug. 1, 2004 (Aug. 1, 2004), pp. 1483-1494.

* cited by examiner

METHOD FOR PREPARING A SAMPLE FOR LASER INDUCED BREAKDOWN SPECTROSCOPY

CROSS-REFERENCE TO RELATED APPLICATIONS

This application is a continuation of U.S. application Ser. No. 17/575,819, filed on Jan. 14, 2022, which is a continuation of U.S. application Ser. No. 17/038,531, filed on Sep. 30, 2020, which is a continuation of and claims priority under 35 U.S.C. §§ 120/121 to U.S. patent application Ser. No. 16/323,572, filed on Feb. 6, 2019, which is a National Stage of PCT/162016/055342, filed on Sep. 8, 2016, the entire contents of each of which are incorporated herein in their entirety.

BACKGROUND

The present invention relates to a method for preparing a sample for laser induced breakdown spectroscopy (LIBS) analysis and in particular to a method of preparing a sample of solid organic material for LIBS analysis.

LIBS is a spectrochemical technique that uses a pulse laser of very short pulse duration (typically between nanoseconds and femtoseconds) which is focused on a sample to create transient temperatures upwards of 10,000 Kelvin.

In this environment, a portion of the sample is converted into plasma and the chemical bonds are broken to produce electronically excited atoms and ions. These excited species give emit radiation at specific wavelengths that depend on the constituent element.

By analysing the light emitted by the plasma it is possible to identify the constituent elements of interest by their characteristic emission wavelengths and to measure the concentration of the constituent elements of interest by measuring the intensity of the light at their characteristic emission wavelengths.

Ideally, the intensity of the characteristic emission wavelength is dependent only on the quantity of the associated constituent element present in the sample. However, it is generally known that variations in sample properties, being variations in physical or chemical properties of the matrix in which the constituent elements are found, affect the intensities of the characteristic emission wavelengths of the associated constituent elements. This problem, generally referred to as "matrix effects", is well known in the art and is a factor that limits LIBS accuracy.

To be properly analyzed using LIBS the samples, among other things, should be homogeneous. Typically samples of naturally occurring organic material, such as plant material samples, are not naturally homogeneous, thus they must be processed into a homogeneous sample. To achieve this, the organic material is first broken down into unconsolidated particles or granules, usually by being ground, shredded or pulverized, and then the granular sample is converted into a single solid unit by forming the granular material into a sample pellet. Forming is typically done by pressing the particulate material into a consolidated unit, by mixing an epoxy or other binder with the sample and curing to form the sample pellet or a combination of both pressing and adding a binder.

However, even using extremely fine powder inhomogeneities in the organic matrix of the sample may often remain. As the size of the granules increase so often does the inhomogeneity of the final sample.

It is known from U.S. Pat. No. 7,663,749 to provide a LIBS system for measuring a quantity of a constituent element of an inhomogeneous sample in which a division of the sample into domains is made using an image acquired by a CCD camera. LIBS analysis then performed for each domain and the concentration of an element of interest for a sample is calculated from the LIBS analysis of each domain and the relative volumes of the domain and the whole sample. By limiting the analysis to various discrete domains any matrix effects are reduced and the overall accuracy of the concentration analysis is improved.

Other LIBS systems, such as the one described in U.S. Pat. No. 8,319,964, employ a first laser to ablate the sample and a second laser to perform LIBS analysis of the ablation plume. This LIBS analysis is typically performed at a location away from the ablation site and a carrier gas transports the ablation plume to the site for LIBS analysis. As the LIBS analysis of the plasma is uncoupled from the ablation event any matrix effects should be reduced.

Such systems are typically more complicated to construct and are thus more expensive.

SUMMARY

It is an aim of the present invention to mitigate matrix effects on LIBS analysis of solid organic material.

According to a first aspect of the present invention there is provided a method for preparing a sample of plant material for laser induced breakdown spectroscopy (LIBS) comprising the steps of obtaining granular organic material; and forming at least a portion of the granular organic material into a sample pellet, such as by press-forming the granular organic material into a consolidated mass; wherein the method further comprises the step of searing the organic material.

In some embodiments the step of searing is performed only on a surface of the sample pellet to be analysed using LIBS.

Searing (also known as charring) of the sample surface induces a thermochemical decomposition of the organic sample matrix. For a subsequent LIBS analysis, the thermochemical decomposition has two effects; 1) the emission lines for minerals are stronger since the elements are more easily ionized; 2) the accuracy for a quantitative elemental abundance analysis is improved since the seared matrices, when comparing different plant materials, have more in common with respect to chemical composition than have the un-seared matrices.

Usefully, but not essentially, the sample pellet is press-formed and re-pressed after such searing of the surface. This provides a compacted, relatively flat, surface for LIBS analysis.

According to a second aspect of the present invention there is provided a method of performing laser induced breakdown spectroscopy (LIBS) comprising the steps of preparing a sample of organic material according to the method of the first aspect of the present invention; directing a laser beam pulse to a seared surface of the sample of organic material to produce a plasma ablation event; and performing a spectroscopic analysis of light emitted from plasma generated in the plasma ablation event to identify constituent elements of interest in the sample of organic material by their characteristic emission wavelengths.

BRIEF DESCRIPTION OF THE DRAWINGS

These and other advantages and features will be better understood from a consideration of the following description of one or more exemplary embodiments of the method and the system according to the present invention made with reference to the drawings of the accompanying figures, of which.

DETAILED DESCRIPTION

Figure 1:
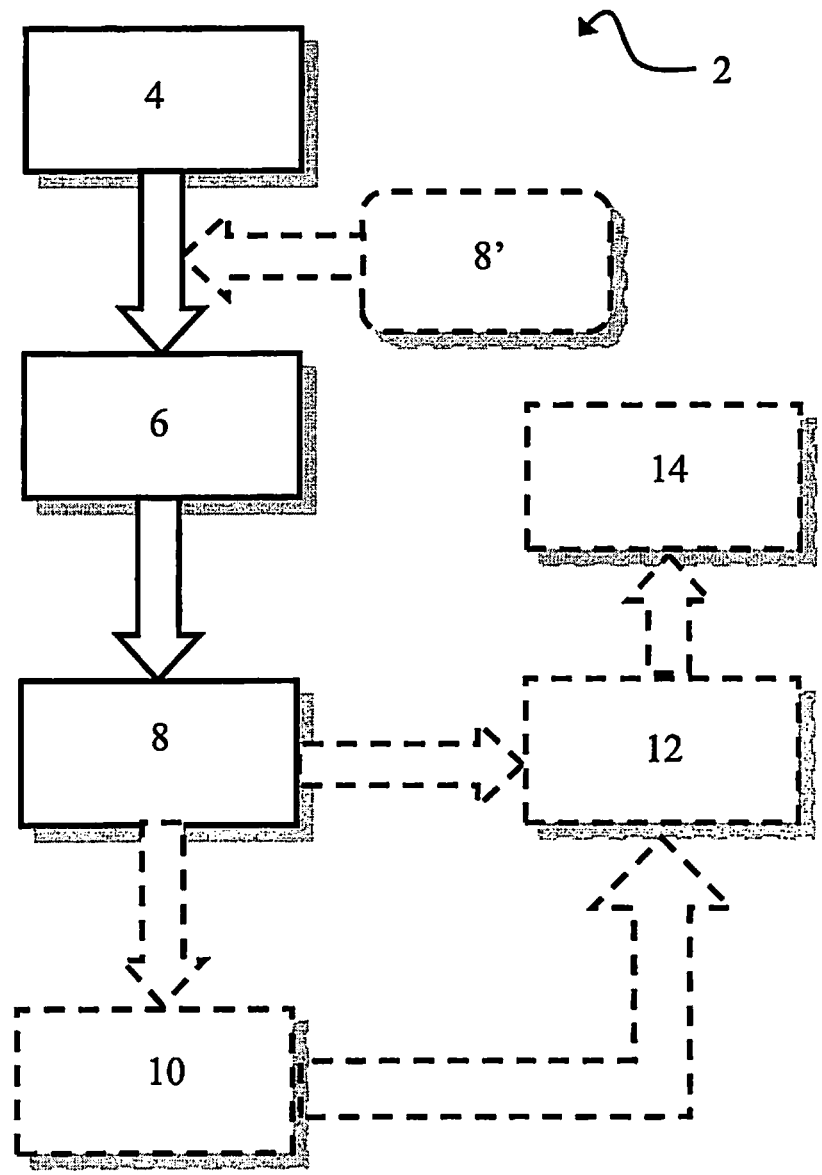
FIG. 1 shows a flow chart illustrating an embodiment of the method of the present invention.

An illustrative embodiment of the method according to the present invention will be described with reference to FIG. 1.

A first step 4 of the method 2 generally consists of obtaining granular organic material. In a particular embodiment a sample of plant material (being material from the plant itself or material manufactured using such material, such as animal feed, flour or foodstuff) is processed into unconsolidated granules, for example by shredding, grinding or pulverizing the material. This processing may be achieved manually, for example using a mortar and pestle, or mechanically, for example using a grinder or shredder, and may be done optionally after the material is dried.

A second step 6 generally consists of forming at least a portion of the granular material obtained at the first step 4 into a sample pellet. In a particular embodiment the granular organic material, for example plant material, is loaded into an open ended cylindrical die and pressure is applied to the material in order to form a sample pellet of consolidated granular plant material which is preferably retained in the die to help maintain structural integrity and to enhance ease of handling. The so-formed pellet presents an exposed end surface, at which LIBS analysis will be performed. A conventional hydraulic laboratory pellet press may be employed to form the sample pellet.

A third step 8 generally consists of searing the granular organic material. In an embodiment this step is performed after the step 6 of forming the sample pellet and involves applying heat only to the exposed end surface of the pellet. In an alternative embodiment the step of searing 8' may be performed on the organic material before the step 6 of forming, for example after the step 4 of obtaining the granular organic material.

A fourth step 10 is performed in embodiments where the step 8 of searing is performed after the step 6 of forming a sample pellet. This fourth step 10 generally consists of pressing (or re-pressing) the sample pellet. At this step 10 pressure is applied to the sample pellet in order to consolidate the material which forms the seared exposed end surface of the sample pellet. The press employed at the step 6 of forming is conveniently employed at this step 10 of pressing (or re-pressing) the sample pellet.

Samples are prepared according to the method (2) described above in respect of FIG. 1 by firstly obtaining granulated plant material (4); then press-forming the granulated plant material into a sample pellet (6) having an exposed end surface for LIBS analysis; then searing the exposed end surface (8); and finally re-pressing the seared exposed end surface (10) before presenting the sample for LIBS analysis. LIBS analysis is performed on the seared exposed end surface of each of the resulting sample pellets. Essentially, this is achieved by directing a laser beam pulse to a seared surface of the sample of organic material to produce a plasma ablation event (12) and performing a spectrometric analysis of light emitted from plasma generated in the plasma ablation event to identify constituent elements of interest in the sample of organic material by their characteristic emission wavelengths (14). Spectra generated by the spectrometer of the LIBS system for seared (solid lines) and un-seared (broken lines) sample pellets are illustrated in FIGS. 2A-2D for sodium (Na) in mixed ration feed (FIG. 2A); for Calcium (Ca) in mixed ration feed (FIG. 2B); for potassium (K) in soy (FIG. 2C) and for phosphorus (P) in soy (FIG. 2D). As can be seen the spectral features associated with the elements in each of the samples are all enhanced in the seared sample pellets.

Figure 2A:
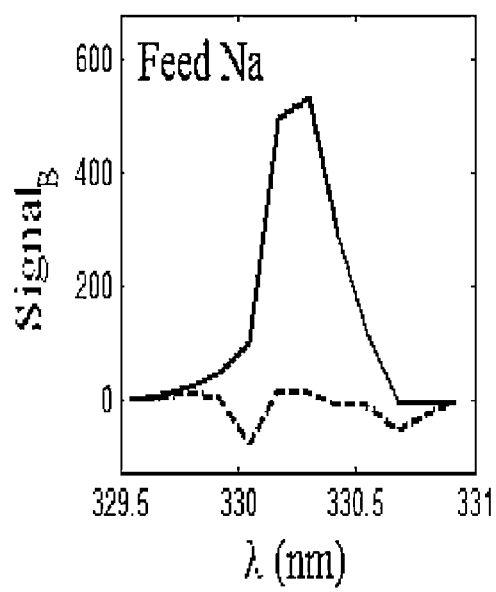
FIGS. 2A-2D show Comparative LIBS spectra of seared and un-seared samples of Feed and Soy.
Figure 2B:
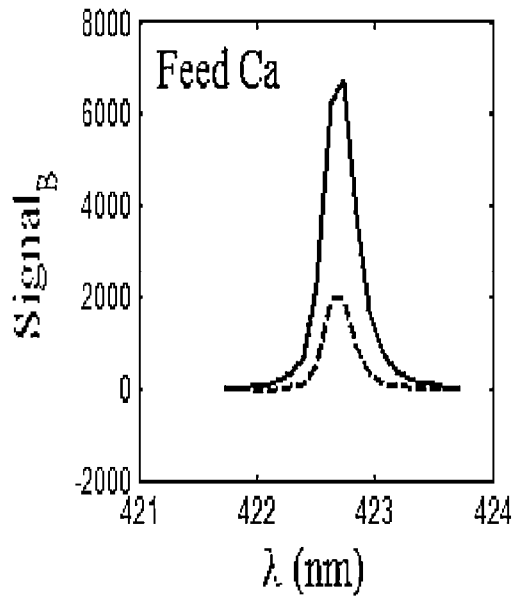
Figure 2C:
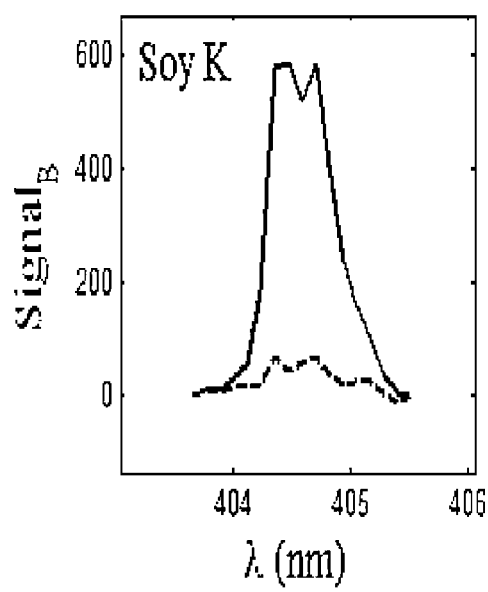
Figure 2D:
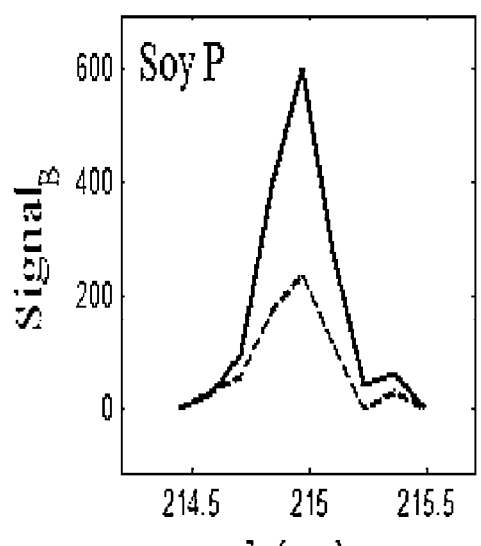
Figure 3:
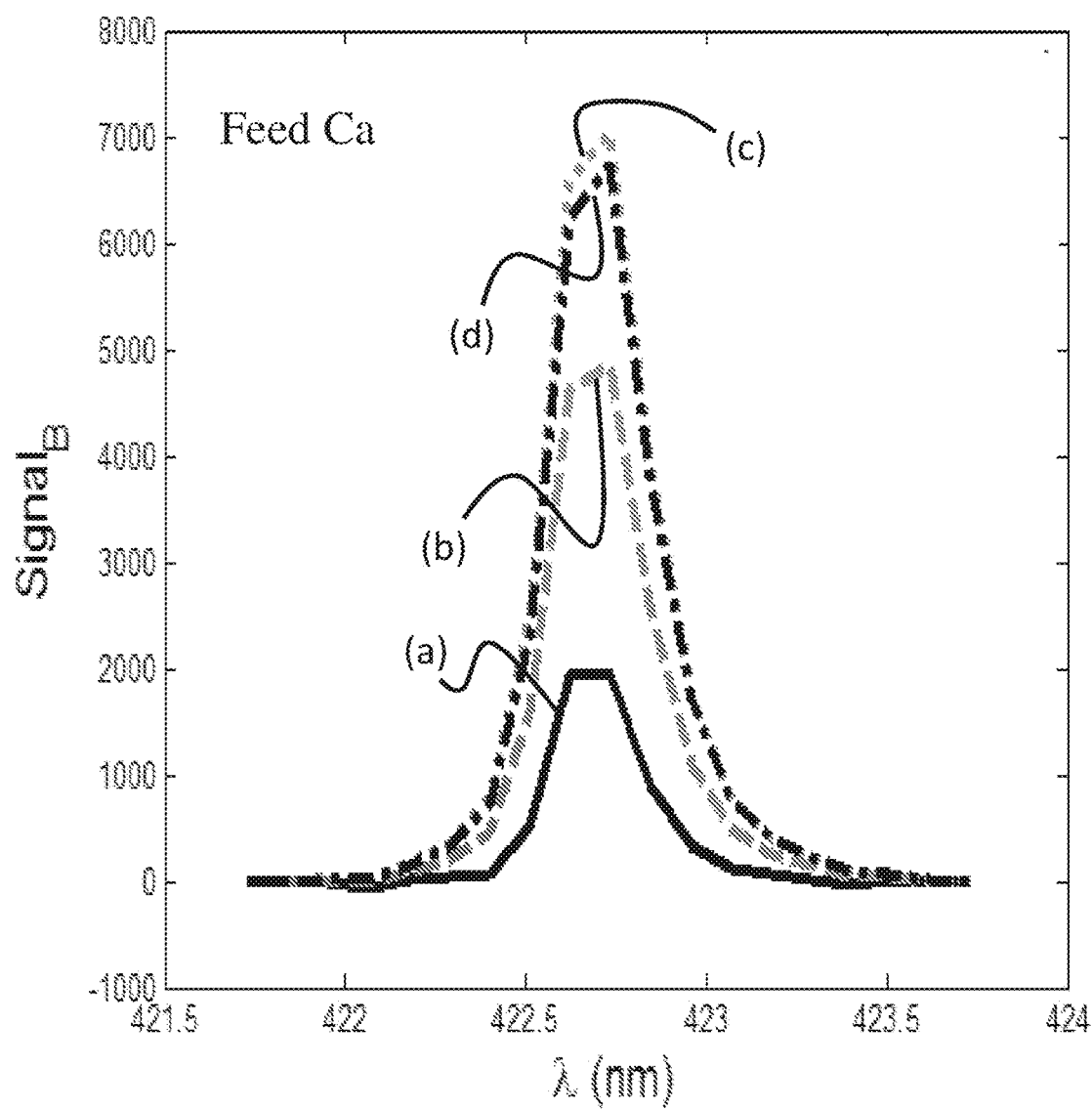
FIG. 3 shows Comparative LIBS spectra of samples of Feed under different searing durations.

The effect of searing duration on LIBS spectra from the seared exposed end surfaces of sample pellets of mixed feed ration produced according to the method of FIG. 1 is illustrated in FIG. 3 for calcium (Ca) and includes the step 10 of re-pressing the sample pellet after searing. Five tons per square centimeter is applied to the plant material in the die for ninety seconds at each pressing stage 2, 10. LIBS analysis 12, 14 is performed at five different searing levels: (a) 'No searing' (i.e. the method according to FIG. 1 is performed up to and including the step 6 of press-forming particulate mixed feed ration into a sample pellet); (b) 'Normal searing' (i.e. searing is stopped when the exposed upper surface of the pellet becomes black according to visual inspection); (c) 'Heavy searing' (twice the searing time compared to Normal searing); and (d) 'Heaviest searing' (three times the searing time compared to Normal searing).

As can be seen from FIG. 3, the intensity of the LIBS spectral signal due to Ca increases as the duration of the searing increases (i.e. from (a) to (c)). The intensities begin to converge as searing intensity increased and beyond a certain searing level (between the Heavy (c) and Heaviest (d) searing durations) the intensity of the LIBS spectral signal begins to reduce. Thus the optimum searing time for a specific matrix and/or searing temperature can be readily experimentally determined.

What is claimed is:

1. A method for preparing a sample of an organic material for laser induced breakdown spectroscopy (LIBS), the method comprising:
    receiving a sample pellet of the organic material, the organic material including an organic matrix, the sample pellet including an end surface; and
    applying heat to the end surface of the sample pellet to sear at least the end surface of the sample pellet to induce a thermochemical decomposition of at least a portion of the organic matrix that is included in the sample pellet, to establish at least a seared end surface of the sample pellet,
    wherein the receiving the sample pellet includes receiving the sample pellet in an open ended cylindrical die such that the end surface of the sample pellet is exposed in the open ended cylindrical die as an exposed end surface, and
    wherein the applying heat to the exposed end surface of the sample pellet sears at least the exposed end surface of the sample pellet that is exposed through the open ended cylindrical die to establish at least the seared end surface of the sample pellet.

2. The method of claim 1, wherein the searing sears only the end surface of the sample pellet.

3. The method according to claim 1, further comprising:
    applying pressure to the sample pellet while the sample pellet is retained in the open ended cylindrical die, subsequently to searing at least the exposed end surface of the sample pellet, to consolidate organic material of at least the seared end surface of the sample pellet.

4. The method according to claim 1, wherein the organic material includes plant material.

5. The method according to claim 4, wherein the organic material includes animal feed, flour, or foodstuff material.

\* \* \* \* \*